US010345209B2

(12) United States Patent
Bridgstock et al.

(10) Patent No.: US 10,345,209 B2
(45) Date of Patent: Jul. 9, 2019

(54) FUSION BEAD TESTING DEVICE AND METHOD OF TESTING A FUSION BEAD

(71) Applicant: CONTROLPOINT LTD, Derbyshire (GB)

(72) Inventors: Eric Bridgstock, Derbyshire (GB); Michael Bailey, Derbyshire (GB); Andrew Walker, Derbyshire (GB); Christopher Jordan, Derbyshire (GB); Philip Jennings, South Yorkshire (GB)

(73) Assignee: CONTROLPOINT LTD, Derbyshire (GB)

(*) Notice: Subject to any disclaimer, the term of this patent is extended or adjusted under 35 U.S.C. 154(b) by 0 days.

(21) Appl. No.: 15/803,329

(22) Filed: Nov. 3, 2017

(65) Prior Publication Data
US 2018/0058991 A1 Mar. 1, 2018

Related U.S. Application Data

(63) Continuation of application No. 14/239,972, filed as application No. PCT/GB2012/000681 on Aug. 23, 2012.

(30) Foreign Application Priority Data

Aug. 24, 2011 (GB) .................................. 1114626.3

(51) Int. Cl.
*G01N 3/08* (2006.01)
*B29C 37/04* (2006.01)
(Continued)

(52) U.S. Cl.
CPC ............... *G01N 3/08* (2013.01); *B29C 37/04* (2013.01); *B29C 65/2092* (2013.01);
(Continued)

(58) Field of Classification Search
CPC ................................... G01N 3/08; G01N 3/20
See application file for complete search history.

(56) References Cited

U.S. PATENT DOCUMENTS

| 4,677,856 A | 7/1987 | Fischer |
| 4,843,884 A * | 7/1989 | House ................... G01N 29/26 73/622 |
| 2011/0123820 A1 | 5/2011 | Shimanuki et al. |

FOREIGN PATENT DOCUMENTS

| DE | 9303625 U1 * | 8/1993 | ............ G01B 21/22 |
| JP | 2010029897 A | 2/2012 | |

(Continued)

OTHER PUBLICATIONS

International Search Report with Written Opinion dated Jul. 11, 2012 for PCT Patent application No. PCT/GB12/000681, 13 pages.
(Continued)

*Primary Examiner* — Jamel E Williams
(74) *Attorney, Agent, or Firm* — Smith IP Services, P.C.

(57) ABSTRACT

A fusion bead testing device is provided for testing the strength of a fusion bead removed from a pipe joint. The testing device comprises a first pressing means for exerting a force against the fusion bead. If the fusion bead splits as a result of the applied force then the fusion bead fails a quality control test and the fusion bead and consequently the pipe joint from which the bead was removed are deemed too weak. The fusion bead testing apparatus comprises an automatic split detection device for detecting a split in the bead.

40 Claims, 9 Drawing Sheets

(51) Int. Cl.
  *B29C 65/20* (2006.01)
  *B29C 65/82* (2006.01)
  *B29C 65/00* (2006.01)
  *G01N 3/20* (2006.01)

(52) U.S. Cl.
  CPC ........ *B29C 65/823* (2013.01); *B29C 65/8253* (2013.01); *B29C 66/1142* (2013.01); *B29C 66/5221* (2013.01); *G01N 3/20* (2013.01); *B29C 66/02245* (2013.01); *B29C 66/9674* (2013.01); *G01N 2203/0296* (2013.01)

(56) References Cited

FOREIGN PATENT DOCUMENTS

WO  2010082977 A1  7/2010
WO  2013027007 A1  2/2013

OTHER PUBLICATIONS

Japanese Office Action dated Jul. 1, 2016 for JP Patent Application No. 2014-526539, 3 pages.
English Translation of Japanese Office Action dated Jul. 1, 2016 for JP Patent Application No. 2014-526539, 3 pages.
Office Action dated Aug. 12, 2016 for U.S. Appl. No. 14/239,972, 11 pages.
Office Action dated Mar. 2, 2017 for U.S. Appl. No. 14/239,972, 14 pages.

* cited by examiner

FUSION BEAD TESTING DEVICE AND METHOD OF TESTING A FUSION BEAD

CROSS-REFERENCE TO RELATED APPLICATIONS

This application is a continuation of application Ser. No. 14/239,972 filed 20 Feb. 2014, which is a national stage under 35 USC 371 of International Application No. PCT/GB2012/000681, filed on 23 Aug. 2012, which claims priority to United Kingdom Application No. 1114626.3, filed on 24 Aug. 2011. The entire disclosure of the Internal Application is incorporated herein by this reference.

The present invention relates to a fusion bead testing device, in particular to a butt fusion bead testing device.

The butt fusion joining method for polyolefin pipes is well known and successful. The butt fusion joining method is illustrated in FIGS. 1 to 6.

In FIG. 1, a first pipe section 1 and a second pipe section 3 are shown having being loaded to into clamps 2. The end 5 of the first pipe section and the end 7 of the second pipe section must be ensured to be clean. FIG. 2 shows a later stage in which a trimmer 4 is inserted to trim the pipe sections 1, 3 squarely. FIG. 3 shows a later stage in which alignment of the pipe sections 1, 3 is checked. FIG. 4 shows a later stage in which a heater 9 is inserted to melt the ends 5, 7 of the pipe sections 1, 3 under controlled pressure and temperature. FIG. 5 shows a later stage in which the molten ends 5, 7 of the pipe sections 1, 3 are joined to form a fused pipe joint 6. A fusion bead 11 is formed around the exterior of the pipe as molten material from each of the pipe sections 1, 3 oozes outwardly from the interface of the pipe sections 1, 3. The fusion bead 11 is unitary and is formed from material from each of the pipe sections 1, 3. The fusion bead 11 can be removed from the fused pipe using a fusion bead removing tool 12, as shown in FIG. 6. A fusion bead is also formed around the interior of the pipe as molten material from each of the pipe sections 1, 3 oozes inwardly from the interface of the pipe sections.

FIG. 7 shows a cross-sectional profile of a typical fusion bead 11 which is formed on the exterior of the pipe joint after it has been removed from the pipe joint. The fusion bead has an interior side 26 which is the side of the fusion bead adjacent to the pipe before the fusion bead was removed from the pipe, and an exterior side 28 which is the outermost side of the fusion bead before the fusion bead was removed from the pipe. A joint interface 30 is formed on the exterior side 28 which is a region of reduced thickness in the centre of the bead. The bead 11 can be considered to be formed in two halves 30A, 30B located laterally on either side of the joint interface 30. The fusion bead is unitary. The fusion bead has a width along a lateral or transverse direction 12 of the bead.

It has been shown by others that the strength between the two halves 30A, 30B of the bead is directly related to the strength of the fused pipe joint 6 itself. Thus, it has been the standard procedure of some companies to cut away the circular bead 11 and apply a twisting force by hand to reveal any lack of fusion strength at the joint interface 30 of the bead 11, as recommended by British Standard EN 12007-2:2000. A twisting method is illustrated in FIG. 8. When executed properly this method is very slow, especially on larger circumference pipes, as it calls for twisting "every few centimeters". Although the bead bend back test is recognized in the UK, many companies twist the bead only a few times, or even not at all. This method is even less common in the rest of the world. There is also a question of repeatability of the test, as it is difficult to apply the same bending moment to each bead tested. There is a lack of objectivity in testing the bead by hand.

Table 1 provides an overview of the hand twist method.

TABLE 1

Evaluation of hand twist method on beads from pipes of standard diameter.
The sole assumption is that each twist tests a 3 cm region.

| | | | | | | | | | |
|---|---|---|---|---|---|---|---|---|---|
| Nominal External Pipe Diameter, mm | 63 | 180 | 250 | 315 | 400 | 500 | 630 | 710 | 900 |
| Pipe Circumference, cm | 20 | 57 | 79 | 99 | 126 | 157 | 198 | 223 | 283 |
| Number of hand twists required by British Standard, testing "every few centimeters" | 7 | 19 | 26 | 33 | 42 | 52 | 66 | 74 | 94 |
| Percentage of bead tested by 3 hand twists | 45% | 16% | 11% | 9% | 7% | 6% | 4% | 4% | 3% |

Problems of the hand twist method include that it may be difficult to twist beads close to their ends. This is especially important for shorter beads. It may also be difficult to apply enough twisting force by hand to thick, cold beads to show splits.

The following additional standards also recommend bead tests: ISO/TS 10839, W1S 4-32-08 and 1S0 21307.

The present invention provides a device and a method for addressing the abovementioned problems.

The present invention provides a fusion bead testing device, as defined in appended independent claim 1. Further option features of the invention are defined in the appended dependent subclaims.

The strength of the fusion bead is related to the strength of the pipe joint from which the fusion bead was removed. Therefore, testing the strength of the fusion bead is also a test of the strength of the fused pipe joint. If the fusion bead splits during testing then this can be used as an indicator that the pipe joint is weak and fails to meet a quality control standard.

Described herein is a mechanical device for testing butt fusion beads having a series of rollers, a number of which are connected to a winding mechanism, and metal disks such that pressure exerted on the moving bead via the disks may cause faulty joints to split, and for this split to be detected by an automatic split detection device. This may be through either electrical contact of brush/stylus on disk, completing an electrical circuit whose presence directly indicates joint failure in that area, or by passing a signal, e.g. light, through the split, which is picked up by a receiver. The device may be coupled to a data logging system which combines the electrical signals with the measured parameters (temperature, pressure, time, etc.) generated by the butt fusion machine and broadcasts the combined data to a dedicated website for analysis. This process of joint data transmission is described in patent GB2361976 (A). The winding mechanism may comprise a cranked handle.

Further described herein is a method of joint testing which depends on the removal of the butt fusion bead and the bending of the joint interface by means of the device described above.

Described herein is a method and equipment for the direct analysis of butt fusion quality. Analysis is undertaken on the removed bead section and makes use of a mechanical splitting tool with an automatic split measuring device connected electrically to a data gathering system. The fusion bead testing device can also be used as a stand-alone device indicating pass or fail only without reference to any additional data gathering system.

The fusion bead testing device described and claimed herein can test a fusion bead which is formed on and removed from the interior of a pipe joint. Alternatively or additionally the fusion bead testing device described and claimed herein can test a fusion bead which is formed on and removed from the exterior of a pipe joint.

The fusion bead testing device may comprise a split detecting device for detecting a split in the fusion bead. The split detection device may comprise a signal emitter and a signal receiver. The signal emitter and the signal receiver may be arranged on opposing sides of the fusion bead in use, and the signal receiver may detect a signal from the signal emitter in the event that a split occurs in the fusion bead. The signal emitter may be an optical emitter and the signal receiver may be an optical receiver. Alternatively, the signal emitter may emit x rays or air pressure as a signal for reception by the signal receiver.

Further advantages and expedient embodiments can be gathered from the appended claims, the description of the figures, and the drawings, in which:

Figure 1:
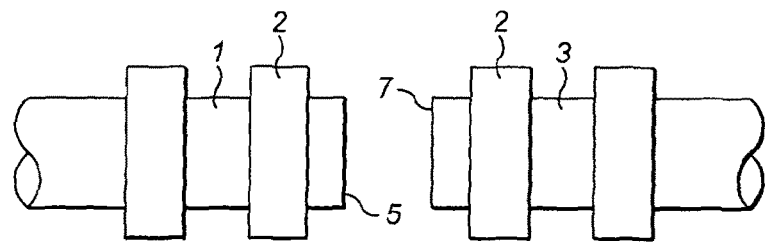
FIG. 1 shows a stage in a well known butt fusion joining method.
Figure 2:
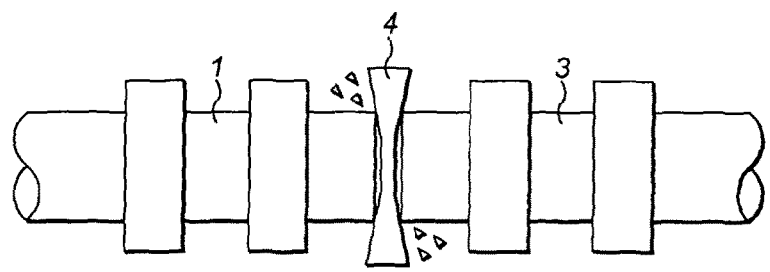
FIG. 2 shows a further stage in a well known butt fusion joining method.
Figure 3:
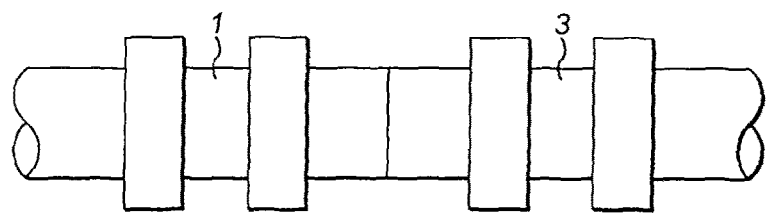
FIG. 3 shows a further stage in a well known butt fusion joining method.
Figure 4:
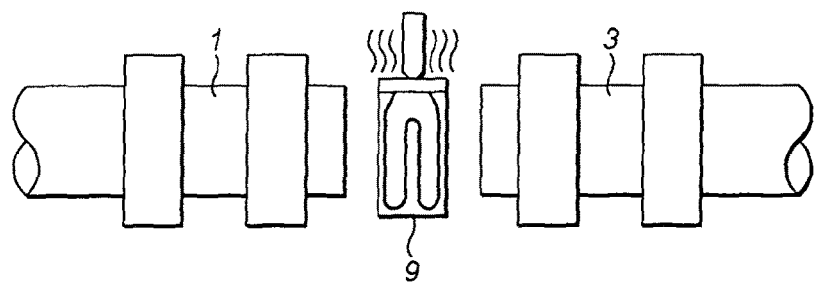
FIG. 4 shows a further stage in a well known butt fusion joining method.
Figure 5:
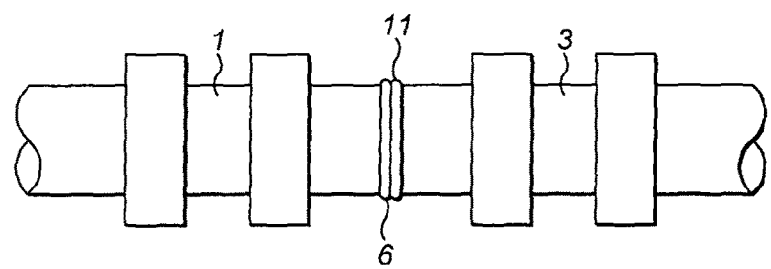
FIG. 5 shows a further stage in a well known butt fusion joining method.
Figure 6:
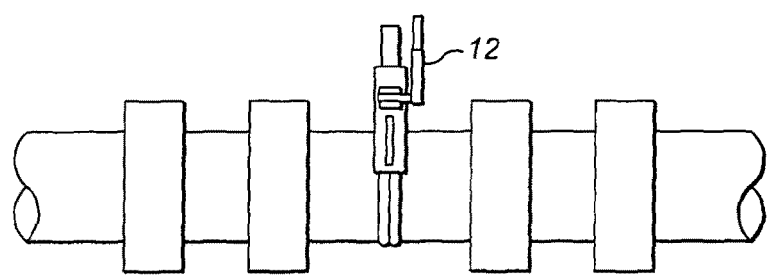
FIG. 6 shows a further stage in a well known butt fusion joining method.
Figure 7:
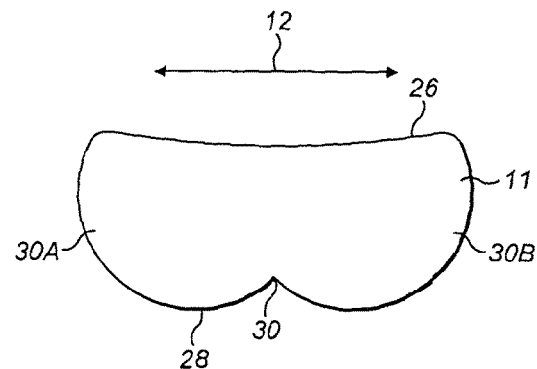
FIG. 7 shows a typical profile of a fusion bead which has been removed from a pipe joint.
Figure 8:
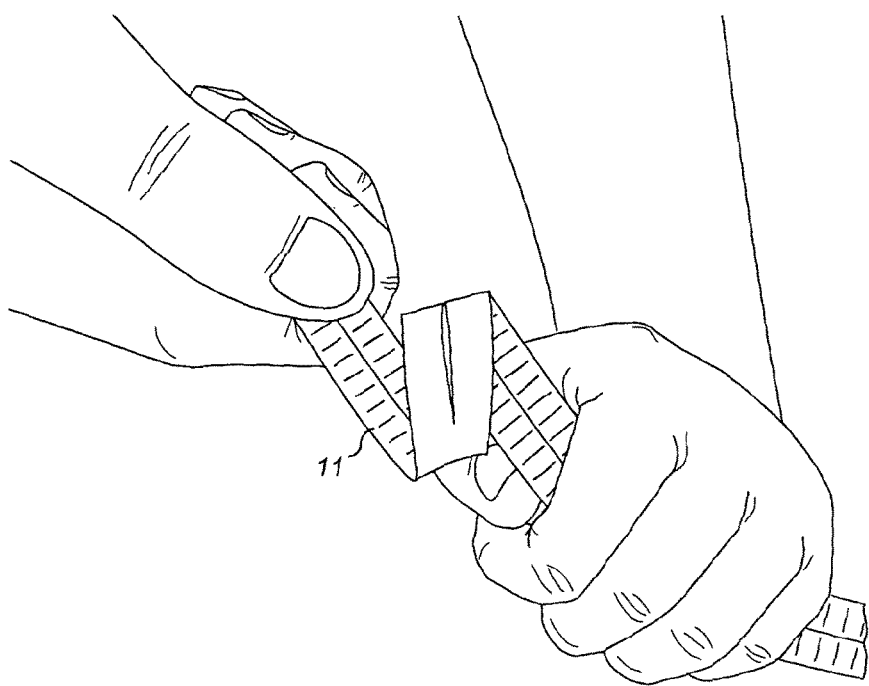
FIG. 8 shows a prior art testing method.
Figure 9:
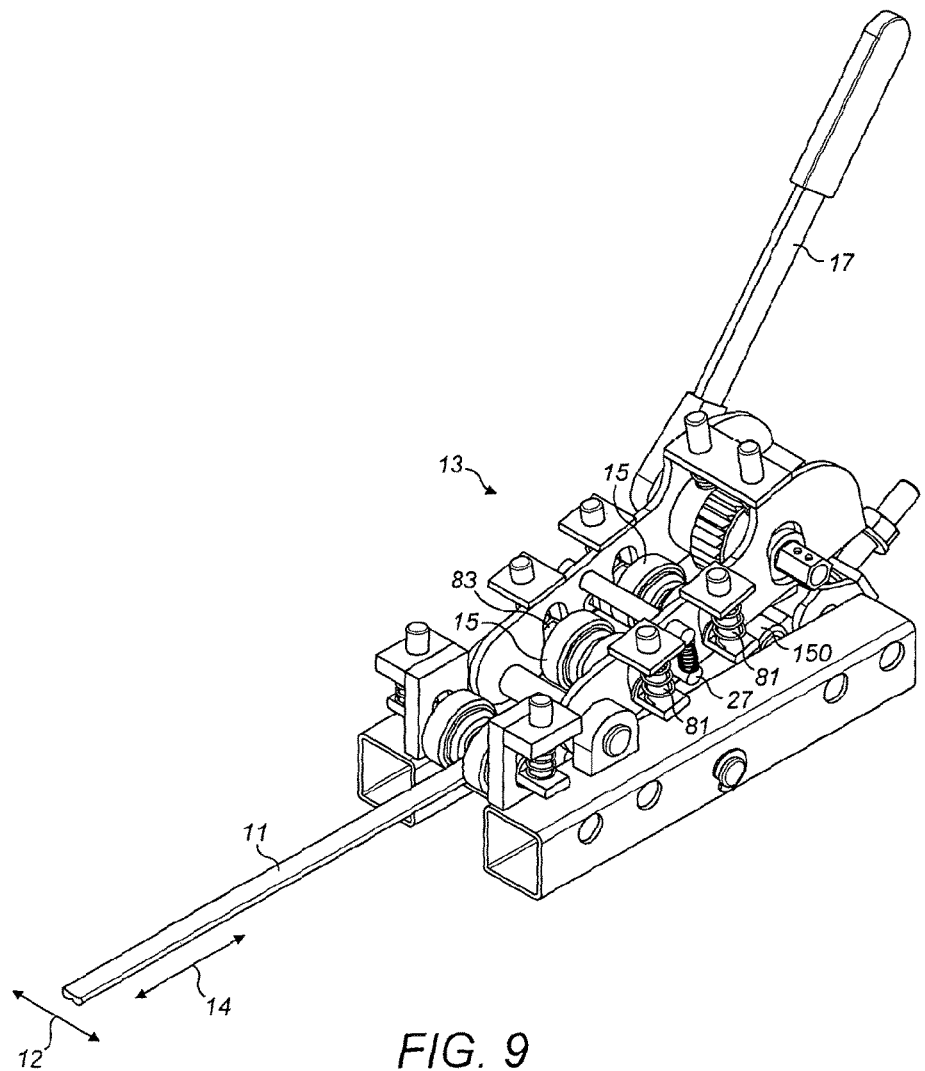
FIG. 9 shows a perspective view of a fusion bead testing device according to the present invention.
Figure 10:
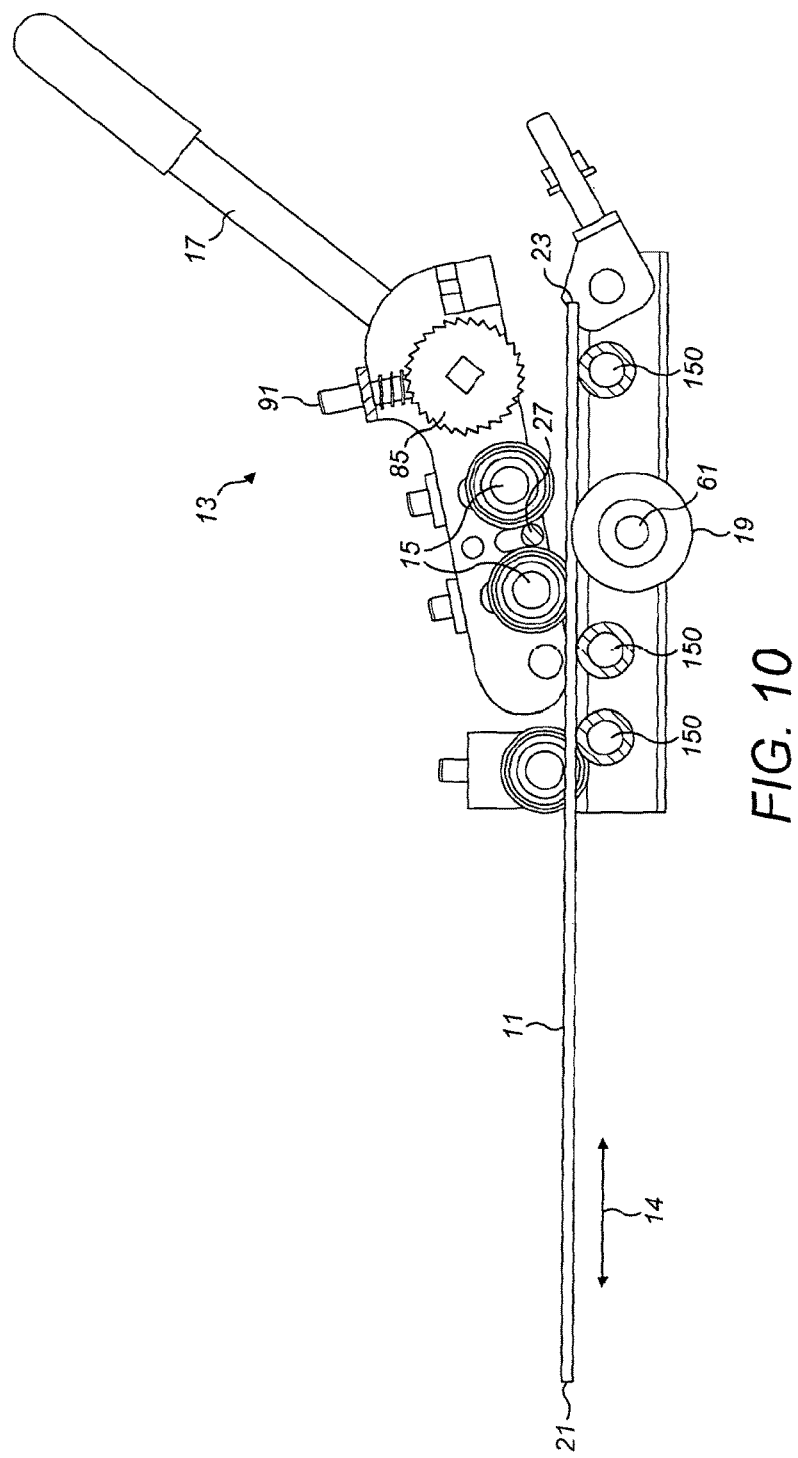
FIG. 10 shows a partial cross-sectional side view of the fusion bead testing device shown in FIG. 9.

In accordance with the present invention, after removal of the bead 11 from the pipe it is fed into a fusion bead testing device 13. The fusion bead testing device 13 is shown in FIGS. 9 and 10. The fusion bead 11 has a length along a longitudinal direction 14 of the bead. The fusion bead 11 has a width along a lateral or transverse direction 12 of the bead.

The fusion bead testing device 13 has a first pressing means 19 for exerting a force on the fusion bead 11. The first pressing means 19 is in the form of a rotatable disk. The disk is rotationally mounted at a mounting point 61. The edge of the disk 19 abuts the joint interface 30 of the fusion bead 11 so that the disk 19 can exert a force at the joint interface 30. The fusion bead testing device is designed so that the fusion bead 11 can be inserted into the device so that the disk 19 alternatively exerts a force on the opposite side of the bead to the joint interface i.e. on the interior side 26 of the bead in the case of testing a fusion bead which is formed on the exterior of a pipe joint.

The fusion bead testing device has a plurality of rollers 15, 150. Two rollers 15 are located on the opposite side of the fusion bead 11 to the disk 19. Three rollers 150 are located on the same side of the fusion bead 11 as the disk 19. The rollers 15, 150 are able to rotate and support the bead 11 as it moves through the device. The rollers 15, 150 are spaced apart in the longitudinal direction 14 for supporting the bead 14 along its length.

Some of the rollers 15 bend the bead around rotatable circular disks 19 in the center of the equipment. These disks 19 apply force along the length of the bead at its center, where the two pipes ends have been fused. Springs 81 are associated with the rollers 15 to bias the rollers towards the fusion bead 11 to press the fusion bead against the disk 19. The rollers 15 are each mounted on an axle 83. Springs 81 exert a force on the axle 83 on either side of the roller.

A toothed wheel 85 is provided. The toothed wheel 85 is fixedly connected to a lever 17. The lever 17 moves when a user pushes down on the free end of the lever to cause the toothed wheel 85 to rotate. Alternatively, another winding mechanism could be used in place of the lever to rotate the toothed wheel 85. When the toothed wheel 85 is driven in rotation by the lever 17, it grips the fusion bead 11 and causes the fusion bead 11 to move through the device 13 in the longitudinal direction 14 as the toothed wheel rotates. The toothed wheel 85 has a width which is similar to or wider than the width of the fusion bead so that the toothed wheel 85 engages the fusion bead across substantially the entire width of the fusion bead 11. A ratchet device 87 is provided which only allows the toothed wheel 85 to rotate in one direction.

The rollers 15 adjacent to the disk 19 press the fusion bead 11 against the disk 19. Both the rollers and the disk 19 exert a force on the bead 11.

The disk 19 exerts a predetermined force against the fusion bead 11, wherein the magnitude of the predetermined force is chosen so that the fusion bead must be able to resist the predetermined force without splitting if the fusion bead is to meet a quality control. If the bead splits under the force applied by the disk 19 then the bead 11, and consequently the fused pipe joint 6 from which the bead was removed, is considered too weak. If the bead 11 does not split then the bead 11, and consequently the fused pipe joint 6 from which the bead was removed, are considered to have suitable strength. The magnitude of the predetermined force which is applied to the bead will vary depending on the required strength of the fused pipe joint 6.

In operation, the entire length of the fusion bead, from its first end 21 to its second end 23, is wound past the disk 19 and consequently the testing force is applied substantially along the entire length of the bead. If a split occurs at any point along the length of the bead then this is considered to be a "fail" and the fused pipe joint from which the bead was removed is indicated to be faulty. If the bead does not split then this is considered to be a "pass" and the fused pipe joint from which the bead was removed is indicated to meet a required quality control.

Figure 11:
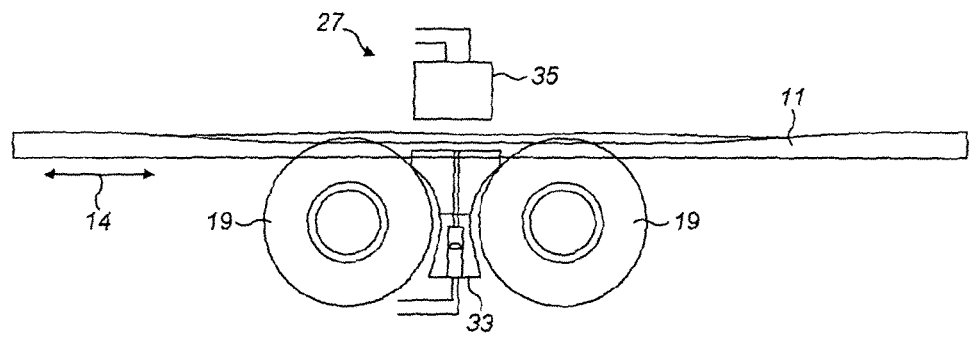
FIG. 11 is a cross-sectional view through the fusion bead testing device shown in FIGS. 9 and 10 showing detail of an automatic split detection device according to a first embodiment.
Figure 12:
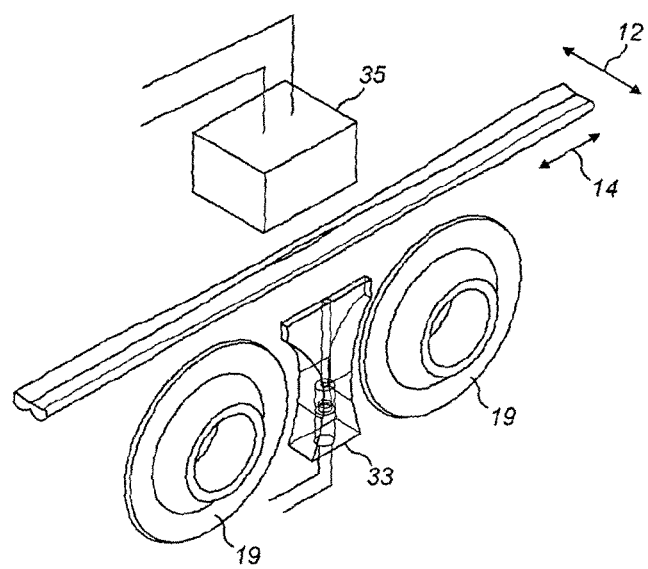
FIG. 12 is an exploded perspective view showing details of the automatic split detection device shown in FIG. 11.

The device has an automatic split detection device 27 for detecting a split in the fusion bead. FIGS. 11 and 12 show detail of the split detection device 27 which comprises an optical emitter 33, for example a LED, and an optical receiver 35. The optical emitter 33 and receiver 35 are positioned on opposite sides of the fusion bead 11. The optical receiver 35 detects light from the optical emitter 33 in the event that a split occurs in the fusion bead. The reception of light provides a signal that the bead has split. If the bead has not split then the bead 11 blocks the light path from the emitter 33 to the receiver 35. A split in the bead 11 is a direct measure of the weakness of the fused pipe joint from which the bead has been removed.

In FIGS. 11 and 12, two disks 19 are provided for exerting a force on the fusion bead 11. The split detection device 27 is located between the two disks 19.

Figure 13:
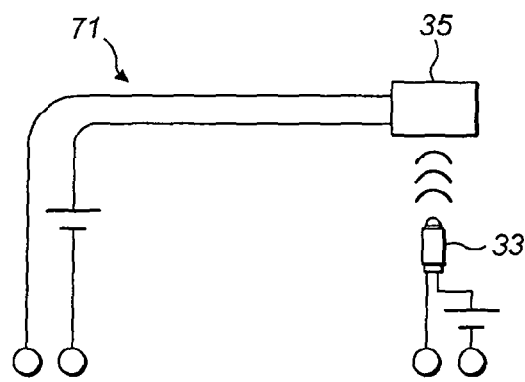
FIG. 13 is a circuit diagram relating to the automatic split detection device shown in FIGS. 11 and 12.

FIG. 13 shows that the optical receiver 35 of FIGS. 11 and 12 is connected in a circuit 71.

Figure 14:
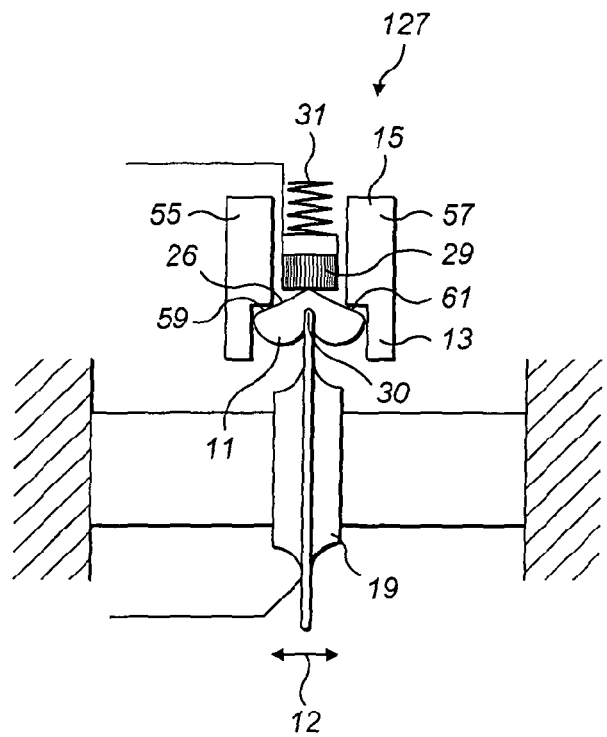
FIG. 14 is a lateral cross-sectional view through a fusion bead testing device according to a further embodiment of the present invention showing detail of an automatic split detection device.
Figure 15:
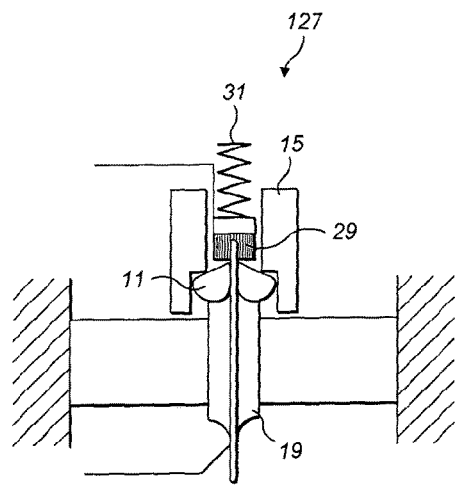
FIG. 15 is a lateral cross-sectional view relating to the further embodiment shown in FIG. 14, in the event that a split occurs in the fusion bead.
Figure 16:
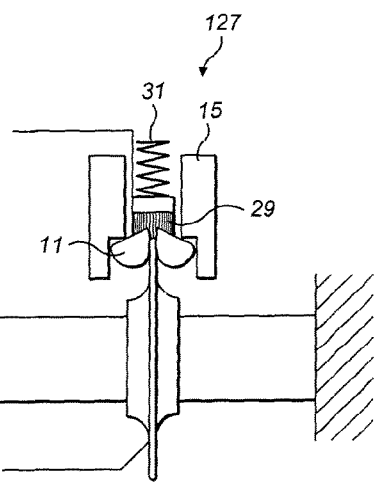
FIG. 16 is a lateral cross-sectional view relating to the further embodiment shown in FIG. 14, in the event that a split occurs in the fusion bead.

FIGS. 14 to 16 show detail of a cross-sectional view of a further embodiment of the fusion bead testing device. The fusion bead testing device of FIGS. 14 to 16 is substantially similar to the fusion bead testing device shown in FIGS. 9 and 10 except an alternative automatic split detection device 127 is provided. In the embodiment shown in FIGS. 14 to 16, the roller 15 presses the fusion bead 11 against the disk 19. The disk 19 abuts the joint interface 30 of the fusion bead. The roller 15 applies a force on the interior side 26 of the fusion bead. The roller 15 has a first part 55 which applies a force at a first point 59 on the fusion bead. The roller 15 has a second part 57 which applies a force at a second point 61 on the fusion bead. The first and second parts 55, 57 are spaced apart in the lateral direction 12 of the bead. The first and second parts 55, 57 are located on either side of the joint interface 30 of the fusion bead. This configuration of the roller 15 and the disk 19 is an especially advantageous arrangement for applying a bending force to bend the fusion bead around its joint interface 30. The roller 15 is biased towards the pressing means 19 with springs 81 (see FIG. 9). Note that this particular configuration of the roller 15 can be utilized in other embodiments of the fusion bead testing device eg. a fusion bead testing device having a different split detection device.

In FIG. 14, the split detection device 127 comprises an electrical conductor in the form of a wire brush 29. The disk 19 is made of an electrically conductive metal and the brush 29 and the disk 19 are arranged on opposite sides of the fusion bead 11. The wire brush 29 and the disk 19 contact one another in the event that a split occurs in the fusion bead (see FIGS. 15 and 16). This closes an electrical circuit 73 (see FIG. 17) and provides a signal that the bead has split. If the bead has not split then the bead 11 prevents the wire brush 29 and the disk 19 from contacting each other. In FIG. 15, the fusion bead 11 has split and the disk 19 passes completely through the fusion bead. The disk 19 makes electrical contact with the brush 29. Note that the roller 15 has moved towards the disk 19 due to the biasing force of the springs 81. In FIG. 16, the fusion bead 11 has split. The roller 15 has not moved significantly towards the disk 19 but the disk 19 still make electrical contact with the brush 29.

A spring 31 biases the wire brush 29 towards the disk 19. Alternatively or additionally, a spring could be provided to bias the disk 19 towards the wire brush 29. The disk 19 and/or the brush 29 may be spring loaded at right angles to the bead direction of travel.

Figure 17:
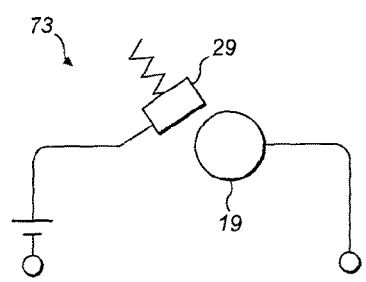
FIG. 17 is a circuit diagram relating to the automatic split detection device of the further embodiment shown in FIGS. 14, 15 and 16.

FIG. 17 shows further detail of the circuit 73 including the wire brush 29 and the disk 19.

Figure 18:
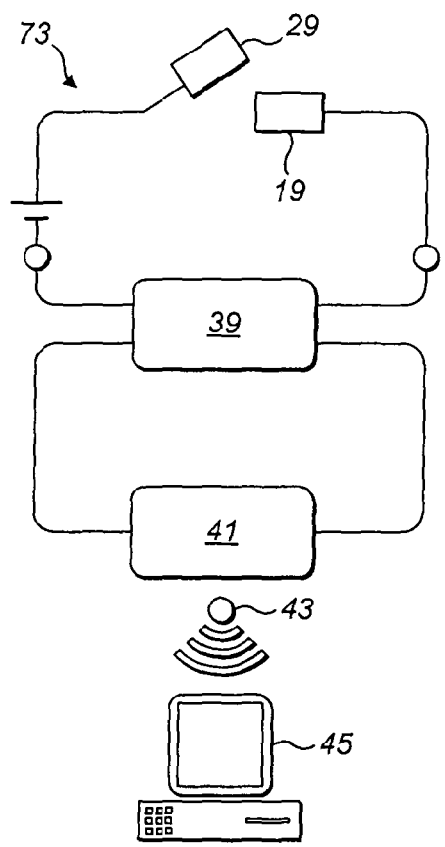
FIG. 18 is a schematic diagram illustrating data transmission for a fusion bead testing device according to the present invention.

FIG. 18 is a schematic diagram showing a wireless transmitter 43 electrically connected to the wire brush 29 and the disk 19 embodiment of the automatic split detection device from FIGS. 14 to 16. Alternatively, the wireless transmitter could be electrically connected to the embodiment of the split detection device 27 shown in FIGS. 11 and 12, which comprises an optical emitter 33 and an optical receiver 35 instead of a wire brush 29 and disk 19. A signal conditioning unit 39 is provided to condition the signal indicating that the bead 11 has split. A telemetry device 41 is provided and associated therewith is a wireless transmitter 43 which transmits the conditioned signal from the circuit to a dedicated website 45. Split bead pass/fail information can therefore be sent to the dedicated website 45. The information transmitted may include detail as to whether or not the bead has split, and optionally the information may additionally include information relating to roller clamp pressure, the length of fusion bead tested, user inputs, the number of splits, the length of each split and the circumferential position of each split in relation to the bead length.

Figure 19:
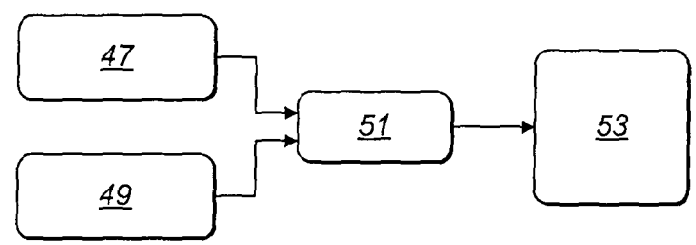
FIG. 19 is a flow diagram illustrating the collation and transfer of information for a fusion bead testing device according to the present invention.

FIG. 19 is a flow diagram showing information flow relating to the fusion bead testing device. A telemetry device 51 can be used to transmit both measured joint parameters 47 generated by the data logging system of the butt fusion machine and split bead pass/fail information 49 to a dedicated website 53 showing real-time data. The dedicated website can also analyse the data and, if necessary, send signals or machine commands back to the butt fusion machine via the telemetry device. The flow of information and signals can therefore be two-way between the fusion bead testing device and the dedicated website.

The invention claimed is:

1. A fusion bead testing device for testing a fusion bead removed from a pipe joint, the fusion bead testing device comprising:
   a first pressing means for exerting a force on the fusion bead;
   a driving means, operation of which causes the fusion bead to move relative to the first pressing means such that the first pressing means exerts a force at a plurality of points along a length of the fusion bead; and
   a split detection device for detecting a split in the fusion bead,
   wherein the split detection device comprises a signal emitter and a signal receiver, wherein the signal emitter and the signal receiver are arranged on opposing sides of the fusion bead in use, and the signal receiver detects a signal from the signal emitter when a split occurs in the fusion bead.

2. The fusion bead testing device according to claim 1, wherein a magnitude of the force is chosen so that the fusion bead must be able to resist the force without splitting for the fusion bead to meet a quality control.

3. The fusion bead testing device according to claim 1, wherein the first pressing means exerts the force on the fusion bead at a joint interface of the fusion bead in operation of the fusion bead testing device.

4. The fusion bead testing device according to claim 3, wherein the first pressing means abuts the joint interface of the fusion bead in operation of the fusion bead testing device.

5. The fusion bead testing device according to claim 1, wherein the first pressing means is arranged for bending the fusion bead around a joint interface of the fusion bead.

6. The fusion bead testing device according to claim 1, further comprising a second pressing means for pressing the fusion bead against the first pressing means.

7. The fusion bead testing device according to claim 6, wherein the second pressing means is arranged to apply the force at a first point on a first side of the fusion bead and at a second point on the first side of the fusion bead.

8. The fusion bead testing device according to claim 7, wherein the second pressing means has a first part for applying the force at the first point and a second part for applying the force at the second point.

9. The fusion bead testing device according to claim 7, wherein the first point and the second point are spaced laterally apart and are located on opposite sides of the joint interface of the fusion bead.

10. The fusion bead testing device according to claim 7, wherein the first side is an interior side of the fusion bead.

11. The fusion bead testing device according to claim 7, further comprising a biasing means for biasing the second pressing means towards the first pressing means.

12. The fusion bead testing device according to claim 11, wherein the biasing means comprises a first spring.

13. The fusion bead testing device according to claim 12, wherein the second pressing means is mounted on an axle, and wherein the first spring exerts a pressing force against the axle.

14. The fusion bead testing device according to claim 13, wherein the biasing means comprises a second spring which exerts a pressing force against the axle, wherein said first spring and said second spring are arranged on opposite sides of the second pressing means.

15. The fusion bead testing device according to claim 6, wherein the second pressing means comprises a roller for pressing the fusion bead against the first pressing means.

16. The fusion bead testing device according to claim 6, further comprising a third pressing means for pressing the fusion bead against the first pressing means.

17. The fusion bead testing device according to claim 16, wherein the third pressing means comprises a roller for pressing the fusion bead against the first pressing means.

18. The fusion bead testing device according to claim 1, further comprising a wheel for engaging the fusion bead to move the fusion bead.

19. The fusion bead testing device according to claim 18, wherein the driving means is configured for rotating the wheel.

20. The fusion bead testing device according to claim 19, wherein the driving means comprises a lever connected to the wheel to rotate the wheel.

21. The fusion bead testing device according to claim 18, further comprising a ratchet device for allowing rotation of the wheel in one direction only.

22. The fusion bead testing device according to claim 1, wherein the first pressing means comprises a disk.

23. The fusion bead testing device according to claim 1, wherein the first pressing means is rotatably mounted for rotation of the first pressing means as the fusion bead moves relative to the first pressing means.

24. The fusion bead testing device according to claim 1, wherein the signal emitter is an optical emitter and the signal receiver is an optical receiver.

25. The fusion bead testing device according to claim 1, further comprising a transmitter connected to the split detection device for transmitting information relating to the fusion bead to a receiver.

26. The fusion bead testing device according to claim 25, wherein the information includes information relating to at least one of the group consisting of: (a) whether the fusion bead has split, (b) a magnitude of force exerted by the first pressing means on the fusion bead, (c) a length of the fusion bead being tested, (d) user inputs, (e) a number of splits, (f) a length of each split and (g) a circumferential position of each split in relation to the fusion bead length.

27. The fusion bead testing device according to claim 25, further comprising a display interface for displaying the information received by the receiver.

28. The fusion bead testing device according to claim 27, wherein the display interface comprises a website.

29. The fusion bead testing device according to claim 25, further comprising a data logging system for recording the information relating to the fusion bead.

30. The fusion bead testing device according to claim 25, wherein the transmitter is a wireless transmitter.

31. The fusion bead testing device according to claim 1, further comprising a further pressing means for exerting the force on the fusion bead, wherein the further pressing means is a metal disk and the first pressing means and the further pressing means exert a pressure on a moving fusion bead such that the pressure exerted on the moving bead via the first pressing means and the further pressing means causes faulty joints to split, wherein the first pressing means is in the form of a metal disk.

32. The fusion bead testing device according to claim 1, further comprising a series of rollers, at least one of the rollers being connected to a winding mechanism, and metal disks such that pressure exerted on the bead via the disks causes faulty joints to split, a faulty joint split being detected by an automatic split detection device.

33. The fusion bead testing device according to claim 32, wherein the split detected by the automatic split detection device is detected by one of: (a) electrical contact which completes an electrical circuit, and (b) a signal passed through the split and picked up by a receiver.

34. The fusion bead testing device according to claim 32, wherein the fusion bead testing device is coupled to a data logging system which combines electrical signals with measured parameters generated by a butt fusion machine and broadcasts the combined electrical signals and measured parameters to a dedicated website for analysis.

35. A fusion bead testing device for testing a fusion bead removed from a pipe joint, the fusion bead testing device comprising:

a first pressing means for exerting a force on the fusion bead;

a driving means, operation of which causes the fusion bead to move relative to the first pressing means such that the first pressing means exerts a force at a plurality of points along a length of the fusion bead; and a wheel for engaging the fusion bead to move the fusion bead, wherein the driving means is configured for rotating the wheel, and wherein rotation of the wheel by the driving means moves the fusion bead relative to the first pressing means.

36. A fusion bead testing method, comprising:

testing a strength of a fusion bead with a fusion bead testing device, the fusion bead testing device comprising a pressing means for exerting a force on the fusion bead, and the fusion bead testing device further comprising a driving means; and the testing comprising operating the driving means to cause the fusion bead to move relative to the pressing means such that the pressing means exerts the force at a plurality of points along a length of the fusion bead, and wherein the testing comprises testing a strength of the fusion bead along substantially the entire length of the fusion bead.

37. The fusion bead testing method according to claim 36, wherein the testing comprises determining whether a split has occurred in the fusion bead.

38. The fusion bead testing method according to claim 36, further comprising transmitting information relating to the fusion bead to a receiver.

39. A fusion bead testing method, comprising:

removing a fusion bead from a fused pipe joint, wherein the removing comprises removing the fusion bead which has formed on at least one of (a) an exterior of the fused pipe joint and (b) an interior of the fused pipe joint; and then testing a strength of the fusion bead with a fusion bead testing device, the fusion bead testing device comprising a pressing means for exerting a force on the fusion bead.

40. The method according to claim 39, wherein the testing comprises determining whether the fused pipe joint meets a required strength based on whether a split occurs in the fusion bead.

* * * * *